(12) United States Patent
Moses et al.

(10) Patent No.: US 7,153,660 B2
(45) Date of Patent: Dec. 26, 2006

(54) NON-INVASIVE ENZYME SCREEN FOR TISSUE REMODELLING-ASSOCIATED CONDITIONS

(75) Inventors: Marsha A. Moses, Brookline, MA (US); Li Yan, Wellesley, MA (US)

(73) Assignee: Children's Medical Center Corporation, Boston, MA (US)

( * ) Notice: Subject to any disclaimer, the term of this patent is extended or adjusted under 35 U.S.C. 154(b) by 182 days.

(21) Appl. No.: 09/977,878

(22) Filed: Oct. 15, 2001

(65) Prior Publication Data

US 2002/0081641 A1   Jun. 27, 2002

Related U.S. Application Data

(60) Provisional application No. 60/240,489, filed on Oct. 13, 2000.

(51) Int. Cl.
| | |
|---|---|
| G01N 33/48 | (2006.01) |
| G01N 33/53 | (2006.01) |
| G01N 33/536 | (2006.01) |
| G01N 33/543 | (2006.01) |
| G01N 33/573 | (2006.01) |

(52) U.S. Cl. .................... 435/7.1; 435/7.4; 435/7.92; 435/23; 436/64; 436/536

(58) Field of Classification Search .............. 435/4, 435/7.1, 7.4, 7.92, 23; 436/64, 536
See application file for complete search history.

(56) References Cited

U.S. PATENT DOCUMENTS 6,037,138 A    3/2000 Moses et al.
6,610,484 B1 *  8/2003 Hung ........................ 435/6

FOREIGN PATENT DOCUMENTS

WO    WO 93/20447     * 10/1993
WO    WO 97/41441 A2   11/1997
WO    WO 97/41441 A3   11/1997

OTHER PUBLICATIONS

The abstract of Black et al (Clinical Cancer Research, Feb. 2000, vol. 6, pp. 467-473).*
Kolkenbrock et al (Biological Chemistry, 1996, vol. 377, pp. 529-533).*
Stoesz et al (International Journal of Cancer, 1998, vol. 79, pp. 565-572).*
Kerr and Thorpe (Immunochemistry LabFax, 1994, pp. 115-122).*
Tsuda et al (FEBS Letters, 1993, vol. 319, pp. 35-39).*
Abstract of Monier et al (Clinica Chimica Acta, Sep. 2000, vol. 299, pp. 11-23).*
Kjeldsen et al (Journal of Biological Chemistry, 1993, vol. 268, pp. 10425-10432).*
Baker, T. et al. "Serum metalloproteinases and their inhibitors: markers for malignant potential." *Br J Cancer.* Sep. 1994; 70(3):506-12.
Garbisa, S. et al. "Correlation of serum metalloproteinase levels with lung cancer metastasis and response to therapy." *Cancer Res.* Aug. 15, 1992; 52(16):4548-9.
Kleiner, D.E. et al. "Matrix metalloproteinases and metastasis." *Cancer Chemother. Pharmacol.* 1999; 43 Suppl:S42-51.
Lochter, A. et al. "The significance of matrix metalloproteinases during early stages of tumor progression." *Ann N Y Acad Sci.* Oct. 23, 1998; 857:180-93.
Monier, F. et al. "Gelatinase isoforms in urine from bladder cancer patients" *Clin. Chim. Acta.* Sep. 2000; 299 (1-2):11-23.
Moses, M. et al. "Increased incidence of matrix metalloproteinases in urine of cancer patients" *Cancer Res.* Apr. 1, 1998; 58(7): 1395-9.
Nakajima, M. et al. "Serum and plasma M(r) 92,000 progelatinase levels correlate with spontaneous metastasis of rat 13762 NF mammary adenocarcinoma." *Cancer Res.* Dec. 1, 1993; 53(23):5802-7.
Yan, Li, et al. "The high molecular weight urinary matrix metalloproteinase (MMP) activity is a complex of gelatinase B/MMP-9 and neutrophil gelatinase-associated lipocalin (NGAL). Modulation of MMP-9 activity by NGAL" *J Biol Chem.* Oct. 5, 2001;276(40):37258-65.
Zucker, S. et al. "Plasma assay of matrix metalloproteinases (MMPs) and MMP inhibitor complexes in cancer. Potential use in predicting metastasis and monitoring treatment." Ann NY Acad. Sci. Sep. 6, 1994; 732:248-62.

* cited by examiner

*Primary Examiner*—Karen A. Canella
(74) *Attorney, Agent, or Firm*—Nixon Peabody LLP (57) ABSTRACT

Methods and kits for diagnosing the presence of and prognosing the appearance of tissue remodelling-associated conditions, involving the presence of enzyme complexes in a biological sample, are disclosed. In particular, the method pertains to diagnosing the presence of or prognosing appearance of metastatic cancer by the identification of high molecular weight enzyme complexes comprising MMPs.

10 Claims, 4 Drawing Sheets

NON-INVASIVE ENZYME SCREEN FOR TISSUE REMODELLING-ASSOCIATED CONDITIONS

RELATED APPLICATIONS

The present application claims priority to U.S. Provisional Application Ser. No. 60/240,489 filed on Oct. 13, 2000.

BACKGROUND OF THE INVENTION

Matrix metalloproteinases (MMP) are a family of endopeptidases whose activities depend on metal ions such as $ZN^{++}$ and $Ca^{++}$. Collectively, MMPs are capable of degrading all the molecular components of extracellular (ECM), the barrier separating the tumor cells from normal surrounding tissues, which is disassembled as part of the metastatic process (Lochter, A. et al. (1998) Ann N Y Acad Sci. 857:180–193). MMPs have been shown to play important roles in a variety of biological as well as pathological processes, especially in tumor cell invasion and metastasis (Kleiner, D. E. and Stelter-Stevenson, W. G. (1999) Cancer Chemother Pharmacol. 43: S42–51). Overproduction of MMps by tumor cells or surrounding stromal cells has been correlated with the metastatic phenotype. In particular, U.S. Pat. No. 6,811,955, the contents of which are herein incorporated by reference in their entirety, teaches that intact and biologically active MMPs can be detected in biological samples of cancer patients and are independent predictors of disease status. The MMP activities detected in U.S. Pat. No. 6,811,955, include, for example, MP-9 (92 kDa, gelatinase B, type IV collagenase, EC3.4.24.35) and MMP-2 (72 kDa, gelatinase A, type IV collagenase, EC3.4.24.24). Both of these MMPs have been shown to be independent predictors of tissue remodeling-associated conditions, e.g., cancer. In addition to these two major gelatinase species, several MMP activities with molecular sizes of equal to, or great than, 150 kDa were observed and were referred to as high molecular weight (hMW) MMPs. Elevated MMP levels in biological fluids, including serum, plasma, and urine from animals bearing experimental tumors or from cancer patients have also been reported in several other studies (Nakajima, M., et al., (1993) (Cancer Res. 53: 5802–7; Zucker, S., et al. (1994) Ann N Y Acad Sci 732: 248–62; Baker, T., et al. (1994) Br J Cancer. 70: 506–12; Garbisa, S., et al. (1992) Cancer Res. 52: 4548–9, 1992).

SUMMARY OF THE INVENTION

With the advances in cancer therapies, early diagnosis and/or prognosis are becoming increasingly important for the disease outcome. Accordingly, the present invention characterizes the molecular identity of hMW MMPs found in biological samples of subjects diagnosed with tissue remodelling-associated diseases, e.g., cancer, and provides early diagnosis/prognosis of such diseases. With the identification of these hMW MMPS, e.g., high molecular weight enzyme complexes, the present invention facilitates the development of non-invasive diagnostic and/or prognostic methods to predict tissue remodelling-associated diseases, such as cancer.

The present invention provides methods and kits for detecting biological markers, e.g., high molecular weight enzyme complexes, to non-invasively monitor the diagnosis and prognosis of tissue remodelling-associated conditions, e.g., cancers. Tissue remodelling-associated conditions encompassed by such methods include diseases such as prostate cancer, breast cancer, ovarian cancer, brain tumors, arthritic conditions, obstructive conditions, and ulcerative conditions. The methods of the instant invention use biological fluid samples, e.g., urine samples, that may be obtained by personnel without medical training, and do not require visiting a clinic or hospital. The statistical association between positive results and occurrence of tissue remodelling-associated conditions are applied to early diagnoses of the appearance of these conditions, and to prognoses of changes in these conditions.

In one embodiment, the present invention provides non-invasive methods for facilitating the diagnosis of a subject for a tissue remodelling-associated condition. Such methods include obtaining a biological sample from a subject, and detecting a high molecular weight enzyme complex in the biological sample. The methods further include correlating the presence or absence of the high molecular weight enzyme complex with the presence or absence of a tissue remodelling-associated condition, thereby facilitating the diagnosis of the subject for a tissue remodelling-associated condition.

In another embodiment, the tissue remodelling-associated condition is cancer, e.g., organ-confined prostate cancer, metastatic prostate cancer, cancer found in cells of epithelial origin, mesodermal origin, endodermal origin or hematopoietic origin, and cancer selected from the group consisting of cancers of the nervous system, breast, retina, lung, skin, kidney, liver, pancreas, genito-urinary tract, and gastrointestinal tract. In another embodiment, the tissue remodelling-associated condition is an arthritic condition, an obstructive condition, or a degenerative condition.

In still another embodiment, the high molecular weight enzyme complex comprises a protease, e.g., a serine protease, e.g., a matrix metalloproteinase, e.g., an MMP-9.

In yet another embodiment, the high molecular weight enzyme complex further comprises a lipocalin, e.g., NGAL, and/or a TIMP, e.g., TIMP-1.

In still another embodiment, the high molecular weight enzyme complex comprises an enzyme complexed with itself to form a multimer, e.g., a dimer or a trimer. Such a multimer can further be complexed with a lipocalin, e.g., NGAL, and/or a TIMP, e.g., TIMP-1.

In still yet another embodiment, the molecular weight of the high molecular weight enzyme complex is at least about 115 kDa to at least about 125 kDa. In another embodiment, the molecular weight of the high molecular weight enzyme complex is at least about 150 kDa.

In another embodiment, the methods of the present invention include obtaining a biological sample from a subject and detecting lipocalin in the biological sample. Such methods further include correlating the presence or absence of the lipocalin with the presence or absence of a tissue remodelling-associated condition, thereby facilitating the diagnosis of the subject for a tissue remodelling-associated condition.

In still another embodiment, the present invention provides kits for facilitating the diagnosis and prognosis of a tissue remodelling-associated condition. Such kits include a container having a reagent for detecting a high molecular weight enzyme complex in a biological sample and instructions for using the reagent for detecting the high molecular weight enzyme complex which facilitates the diagnosis and prognosis of a tissue remodelling-associated condition.

DESCRIPTION OF THE FIGURES

FIG. 1 shows a substrate gel electrophoresis and NGAL Western blot analysis of urine samples. A. Substrate gel electrophoresis of MMPs in urine samples: 50 μl of untreated urine samples were analyzed for MMP activities. Four major gelatinase activities were detected with apparent molecular masses of approximately 200,000, 125,000, 92,000, and 72,000. Their identities are marked with arrows on right. The molecular size markers are Perfect Protein Markers (Novagen, Madison, Wis.) with sizes of 150 kDa, 100 kDa, 75 kDa, and 50 kDa (arrows on left). B. 20 μg of concentrated urine samples were separated on a 4–15% SDS-PAGE gel under non-reducing conditions. Western blot analysis was carried out using a polyclonal antibody against human NGAL. The molecular size markers are Kaleidoscope Prestained Standards (Bio-Rad, Hercules, Calif.) with sizes of 126 kDa, 90 kDa, 44 kDa, 34 kDa, and 17 kDa (arrows on left).

FIG. 4 shows reconstitution of MMP-9/NGAL complexes in vitro. A. Recombinant human MMP-9 and NGAL were diluted in gelatinase buffers with different pH values and were subsequently mixed in a molar ratio of 1:10 (proMMP-9 to NGAL). In vitro reconstitution was carried out at 37° C. for one hour. 10 μM proMMP-9 was loaded in each lane. Purified human neutrophil MMP-9/NGAL was included as a control. B. Recombinant human MMP-9 and NGAL were diluted in normal urine containing no MMP activities and were subsequently mixed in different molar ratios (proMMP-9 to NGAL=2:1, 1:5, 1:10, 1:20). After one hour incubation at 37° C., MMP-9/NGAL complex formation was analyzed using substrate gel electrophoresis. The positions of the 125 kDa and 115 kDa MMP-9/NGAL activity are respectively denoted with the arrow and the arrowhead on right. The molecular size markers are Perfect Protein Markers (Novagen, Madison, Wis.) with sizes of 150 kDa, 100 kDa, 75 kDa, and 50 kDa (arrows on left).

DETAILED DESCRIPTION OF THE INVENTION

The present invention features non-invasive methods for facilitating the diagnosis of a subject for a tissue remodelling-associated condition (TRAC), especially cancers, obstructive and degenerative conditions, and arthritic conditions. Detection of a pattern of enzyme complexes, e.g., high molecular weight (hMW) enzyme complexes, in a biological sample from a subject is used to facilitate diagnosis and prognosis of a TRAC.

The language "high molecular weight enzyme complex" includes an enzyme associated with or bound to another molecule wherein the complex has a high molecular weight allowing it to be used for its intended function of the present invention. Examples of enzyme complexes include, among others, an enzyme bound to another enzyme, an enzyme bound to an enzyme inhibitor, and an enzyme bound to a protein binding molecule, e.g., a lipocalin. Enzyme complexes which comprise enzymes bound to themselves, e.g., multimers, e.g., dimers and trimers, are also encompassed by the present invention.

High molecular weight enzyme complexes include enzyme complexes which have a molecular weight of at least about 115 kDa, e.g., at least about 120 kDa, e.g., at least about 125 kDa, e.g., at least about 130 kDa, e.g., at least about 135 kDa, and, e.g., at least about 140 kDa. High molecular weight enzyme complexes which have a molecular weight of at least about 145 kDa, e.g., at least about 150 kDa, and greater than 150 kDa are also included.

The ranges of high molecular weight values intermediate to those listed also are intended to be part of this invention, e.g. at least about 115 kDa to at least about 120 kDa, at least about 120 kDa to at least about 125 kDa, at least about 125 kDa to at least about 130 kDa, at least about 130 kDa to at least about 135 kDa, at least about 135 kDa to at least about 140 kDa, at least about 140 kDa to at least about 145 kDa, and at least about 145 kDa to at least about 150 kDa. For example, ranges of high molecular weight values using a combination of any of the above values recited as upper and/or lower limits are intended to be included.

In one embodiment of the invention, the high molecular weight enzyme complex does not have a molecular weight of 115 kDa. In another embodiment, the high molecular weight enzyme complex does not include NGAL. In another embodiment, the high molecular weight enzyme complex does not include a progelatinase B enzyme. In yet another embodiment of the invention, the high molecular weight enzyme complex does not include a progelatinase B enzyme associated with NGAL.

The term "enzyme" is art recognized and includes protein catalysts of chemical reactions. Enzymes can be a whole intact enzyme or portions or fragments thereof. The enzymes encompassed by the enzyme complexes of the current invention include naturally occurring enzymes that catalytically degrade proteins, i.e. the enzymes known as proteases or proteinases. By proteinase is meant a progressive exopeptidase that digest proteins by removing amino acid residues from either the N terminal or C terminal which reaction proceeds to achieve significant degradation, or an endopeptidase which destroys the amide bond between amino acid residues with varying degrees of residue specificity. The term "protease" may also include the highly specific amino acid peptidases that remove a single amino acid from an N terminus or C terminus of a protein. Examples are alanine aminopeptidase (EC 3.4.11.2) and leucine aminopeptidase (EC 3.4.11.1), which remove alanine or leucine, respectively, from the amino terminus of a protein that may have alanine and leucine, respectfully, at the amino terminus. The molecular weights of the enzymes comprising the enzyme complexes of the invention include, but not limited to, molecular weights in the range of approximately 72 kDa, approximately 92 kDa, approximately 115 kDa to approximately 125 kDa and approximately 150 kDa or greater. The term "enzyme" includes polymorphic variants that are silent mutations naturally found within the human population.

In one embodiment, the enzyme complexes of the present invention comprise proteases or proteinases. The term proteases (and its equivalent term proteinases) is intended to include those endopeptidases and progressive exopeptidases that are capable of substantially reducing the molecular weight of the substrate and destroying its biological function, especially if that biological function of the substrate is to be a structural component of a matrix barrier. Amino acid peptidases such as alanine aminopeptidase and leucine aminopeptidase are also broadly included among proteases, however do not share the property of significantly reducing the molecular weight of the substrate protein.

Many thousands of proteases occur naturally, and each may appear at different times of development and in different locations in an organism. The invention herein features enzymes of the class of the matrix metalloproteinases (MMPs, class EC 3.4.24). These enzymes, which require a divalent cation for activity, are normally expressed early in the development of the embryo, for example, during hatching of an zygote from the zona pellucida, and again during the process of attachment of the developing embryo to the inside of the uterine wall. Enzyme activities such as N-acetylglucosaminidase (EC 3.2.1.50) appear in urine in the case of renal tubular damage, for example, due to diabetes (Carr, M. (1994) *J. Urol.* 151(2):442–445; Jones, A., et. al. (1995) *Annals. Clin. Biochem.*, 32:68–62). That these activities appear in urine as a result of renal tubular damage is irrelevant to the present invention as described herein.

The term "matrix-digesting enzyme" includes an enzyme capable of digesting or degrading a matrix, e.g., a mixture of proteins and proteoglycans that comprise a layer in a tissue on which certain types of cells are found. Matrix-digesting enzymes are expressed during stages of normal embryogenesis, pregnancy and other processes involving tissue remodelling. In addition, some of these enzymes, for example some matrix metalloproteinases (MMPs), degrade the large extracellular matrix proteins of the parenchymal and vascular basement membranes that serve as mechanical barriers to tumor cell migration. These MMPs are produced in certain cancers and are associated with metastasis (Liotta, L. A., et al. (1991) *Cell* 64:327–336). Examples of MMPs are the type IV collagenases, e.g., MMP-2 (gelatinase A. EC 3.4.24.24) and MMP-9 (gelatinase B, 3.4.24.35), and stromelysins (EC 3.4.24.17 and 3.4.24.22). Some MMPs are specifically inhibited by molecules called tissue inhibitors of metalloproteinases (TIMPs, Woessner, J. F., Jr. (1995) *Ann. New York Acad. Sci.*, 732:11–21),which also may be over produced by tumor cells, however under certain conditions enzyme activity is in molar excess over the TIMPs (Freeman, M. R. et al. (1993) *J. Urol.* 149:659; Lu, X. et al. (1991) *Cancer Res.* 51:6231–6235;Kossakowska, A. E. et al. (1991) *Blood* 77:2475–2481). Accordingly, in one embodiment of this invention, the enzyme complexes of the present methods comprise an inhibitor of the enzyme (TIMPS, e.g., TIMP-1 or TIMP-2). The detection of an inhibitor can be accomplished using art-recognized techniques. Many of MMPs are translated as proenzymes, and may be found in a variety of structures, with ranges of molecular weights including smaller forms (45 kDa, 55 kDa, 62 kDa), and larger forms (72 kDa, 82 kDa, 92 kDa, and higher polymers such as 150 kDa and greater).

In another embodiment of the invention, the high molecular weight enzyme complex comprises a protein binding molecule, e.g., a lipocalin. Lipocalins are small secreted proteins that bind small, hydrophobic molecules to form molecular complexes. Lipocalins are implicated in a variety of functions including, among others, regulation of the immune response, e.g., lipocalins can exert certain immunomodulatory effects in vitro. It has been shown that neutrophil lipocalin covalently attaches to human neutrophil gelatinase (type IV collagenase) thus forming Neutrophil Gelatinase-Associated Lipocalin (NGAL) (Treibel et al. (1992) and Kjelsen et al. (1993)) although most of the protein is secreted in uncomplexed form. These authors prose a regulatory role for NGAL on the action of the gelatinase.

In another embodiment, the present invention includes methods of detecting a lipocalin, e.g., NGAL, as an indicator of a TRAC. Such lipocalins can be detected in a biological sample as an isolated lipocalin or as multimers of lipocalins, e.g., dimers and trimers.

The tissue remodelling conditions that can be monitored by the methods of this invention include a variety of types of cancer; moreover, the enzymes are suitable for diagnosis of other tissue remodelling conditions, such as arthritis, degenerative conditions, and obstructive conditions. The invention provides non-invasive methods for diagnosing these conditions by assay for enzyme complexes, e.g., hMW enzyme complexes, in biological fluids.

The methods of this invention embody detection of enzymes in urine, for diagnosis and prognosis of cancer. The invention also relates to diagnosis and prognosis of metastatic prostate cancer. The varieties of cancer suitable for diagnosis by the methods of this invention include, among others, cancers of epithelial origin, for example, cancers of the nervous system, breast, retina, lung, skin, kidney, liver, pancreas, genito-urinary tract, ovarian, uterine and vaginal cancers, and gastrointestinal tract cancers, which form in cells of epithelial origin. Using the methods described here, cancers of mesodermal and endodermal origin, for example, cancers arising in bone or in hematopoietic cells, are also diagnosed.

The term "subject," as used herein, includes a living animal or human in need of diagnosis or prognosis for, or susceptible to, a condition, in particular an "tissue remodelling-associated condition" as defined below. The subject is an organism capable of responding to tissue remodelling signals such as growth factors, under some circumstances, the subject is susceptible to cancer and to arthritis. In one embodiment, the subject is a mammal, including humans and non-human mammals such as dogs, cats, pigs, cows, sheep, goats, horses, rats, and mice. In one embodiment, the subject is a human. The term "subject" does not preclude individuals that are entirely normal with respect to tissue remodelling-associated conditions or normal in all respects. The subject may formerly have been treated surgically or by chemotherapy, and may be under treatment by hormone therapy or have been treated by hormone therapy in the past.

The term "patient," as used herein, includes a human subject who has presented at a clinical setting with a particular symptom or symptoms suggesting one or more diagnoses. A patient may be in need of further categorization by clinical procedures well-known to medical practitioners of the art (or may have no further disease indications and appear to be in any or all respects normal). A patient's diagnosis may alter during the course of disease progression, such as development of further disease symptoms, or remission of the disease, either spontaneously or during the course of a therapeutic regimen or treatment. Thus, the term "diagnosis" does not preclude different earlier or later diagnoses for any particular patient or subject. The term "prognosis" includes an assessment for a subject or patient of a probability of developing a condition associated with or otherwise indicated by presence of one or more enzymes in a biological sample, e.g., in urine.

The term "biological sample" includes biological samples obtained from a subject. Examples of such samples include urine, blood taken from a prick of the finger or other source such as intravenous, blood fractions such as serum and plasma, feces and fecal material and extracts, saliva, cerebrospinal fluid, amniotic fluid, mucus, and cell and tissue material such as cheek smear, Pap smear, fine needle aspiration, sternum puncture, and any other biopsied material taken during standard medical and open surgical procedures.

The term "invasiveness" as used here with respect to metastatic cancer (Darnell, J. (1990) *Molecular Cell Biology*, Third Ed., W. H. Freeman, NY) is distinct from the use of the term "invasive" to describe a medical procedure, and the distinction is made in context. "Invasive" for a medical procedure pertains to the extent to which a particular procedure interrupts the integrity of the body. "Invasiveness" ranges from fully non-invasive, such as collection of urine or saliva; to mildly invasive, for example a Pap smear, a cheek scrape or blood test, which requires trained personnel in a clinical setting; to more invasive, such as a sternum marrow collection or spinal tap; to extensively invasive, such as open surgery to detect the size and nature of tumors by biopsy of material, taken for example during brain surgery, lung surgery, or transurethral resection in the case of prostate cancer.

Cancer or neoplasia is characterized by deregulated cell growth and division. A tumor arising in a tissue originating from endoderm or exoderm is called a carcinoma, and one arising in tissue originating from mesoderm is known as a sarcoma (Darnell, J. (1990) *Molecular Cell Biology, Third Ed.*, W. H. Freeman, NY). A current model of the mechanism for the origin of a tumor is by mutation in a gene known as an oncogene, or by inactivation of a second tumor-suppressing genes (Weinberg, R. A. (September 1988) *Scientific Amer.* 44–51). The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny. Examples of cancers include cancers of the nervous system, breast, retina, lung, skin, kidney, liver, pancreas, genito-urinary tract, gastrointestinal tract, cancers of bone, and cancers of hematopoietic origin such as leukemias and lymphomas. In one embodiment of the present invention, the cancer is not a cancer of the bladder.

An arthritic condition such as rheumatoid arthritis is an example of a TRAC since the disease when chronic is characterized by disruption of collagenous structures (J. Orten et al. (1982) *Human Biochemistry, Tenth Ed.*, C. V. Mosby, St. Louis, Mo.). Excess collagenase is produced by cells of the proliferating synovium. Other TRAC conditions such as ulcerative, obstructive and degenerative diseases are similarly characterized by alterations in the enzymes of metabolism of structural proteins.

The term "electrophoresis" is used to indicate any separation system of molecules in an electric field, generally using an inert support system such as paper, starch gel, or polyacrylamide. The electrophoresis methods with polyacrylamide gels and the sodium dodecyl sulfate denaturing detergent are described in the Examples below. The protocols are not intended to exclude equivalent procedures known to the skilled artisan. Other SDS polyacrylamide procedures, known to the skilled artisan, may be used, e.g., a single polyacrylamide concentration such as 10%, may be substituted for the gradient in the separation gel. The physical support for the electrophoretic matrix may be capillary tubes rather than glass plates. Details of several SDS-polyacrylamide gel electrophoresis systems are described in many review articles and biotechnology manuals (e.g., Maniatis, T., *Molecular Cloning: A Laboratory Manual*, 2nd Edition, Cold Spring Harbor Press, Cold Spring Harbor, N.Y.). The method is not limited to use of SDS and other detergents. Further, electrophoresis in the absence of detergents may be employed. Proteins may be separated under non-denaturing conditions, for example in the presence of urea on a polyacrylamide matrix (Maniatis, supra), or by charge, for example by the procedure of isoelectric focussing.

In using an electrophoretic technique for separation of enzymes, the electrophoretogram may be developed as a zymogram. The term "zymography" is meant here to include any separations system utilizing a chemically inert separating or support matrix, that allows detection of an enzyme following electrophoresis, by exposing the matrix of the separations system to conditions that allow enzyme activity and subsequent detection. More narrowly, the term zymography designates incorporation of an appropriate substrate for the enzyme of interest into the inert matrix, such that exposing the matrix to the conditions of activity after the electrophoresis stop yields a system to visualize the precise location, and hence the mobility, of the active enzyme. By techniques well-known to the skilled artisan, the molecular weights of proteins are calculated based on mobilities derived from positions on a zymogram. Such techniques include comparison with molecular weight standards, the mobilities of which are determined from general protein stains or from pre-stains specific to those standards, and comparison with positive controls of purified isolated enzymes of interest, which are visualized by the technique of the zymogram, i.e., enzyme activity.

In particular, substrates for detection of proteases by zymography are included in the electrophoresis matrix. For type IV collagenases, the natural substrate is a type IV collagen and gelatin, a type I collagen derivative, is used for the zymography substrate in the Examples presented herein. However other proteins that are suitable for detection of further proteases of interest in TRAC diagnosis, for example, include fibronectin; vitronectin; collagens of types I through III and V through XII; procollagens; elastin; laminin; plasmin; plasminogen; entactin; nidogen; syndecan; tenascin; and sulfated proteoglycans substituted with such saccharides as hyaluronic acid, chondroitin-6-sulfate, condroitin-4-sulfate, heparan sulfate, keratan sulfate, and dermatan sulfate and heparin. Further, convenient inexpensive substrate proteins such as casein, which may not be the natural target of a protease of interest, but are technically appropriate, are included as suitable substrate components of the zymography techniques of the present invention. Chemically synthesized mimetics of naturally occurring protein substrates are also potential zymography substrates, and may even be designed to have favorable properties, such chromogenic or fluorogenic ability to produce a color or fluorescent change upon enzymatic cleavage.

Zymography may be adapted to detection of a protease inhibitor in the biological sample. Since a variety of natural MMP inhibitors are elaborated, such as TIMP-1 and TIMP-2, and are found to be deregulated during TRAC situations, the present invention includes detection of enzyme complexes which comprise enzyme inhibitors, e.g., TIMPs. Thus for example, a "reporter enzyme" for which an enzyme inhibitory activity is being measured, may be incubated with each biological sample obtained by subjects and patients, in one or more quantities corresponding to one or more aliquots of sample, prior to electrophoresis. This enzyme is omitted from one aliquot of the biological sample. The inhibitory presence in the sample is detected as disappearance or decrease of the reporter enzyme band from the developed zymogram. Alternatively, functional enzyme activity assays which include in the reaction mix a known level of active enzyme, to which is added aliquots of experimental samples with putative inhibitory activity, can detect the presence of inhibitors.

Further, the enzymes of tissue remodelling extend to enzyme activities beyond those of proteolytic activity. For example, enzymes that are substituted with residues such as glycosyl, phosphate, sulfate, lipids and nucleotide residues (e.g. adenyl) are well-known to those skilled in the art. These residues are in turn added or removed by other enzymes, e.g., glycosidases, kinases, phosphatases, adenyl transferases, etc. Convenient detection methods for the presence of such activities for TRAC diagnosis and prognosis are readily developed by those with skill in the art, and are intended to comprise part of the invention here.

The zymogram as described in the Examples herein is developed by use of a general stain for protein, in this case, Coomassie Blue dye. The development is possible with general protein stains, e.g., Amido Black dye, and SYPRO Orange stain (Biorad Laboratories, Hercules, Calif. 94537). Further, enzyme activity may be detected by additional techniques beyond that of a clear zone of digestion in a stained matrix, for example, by absence of areas of radioactivity with a radio-labelled substrate, by change in mobility of a radio-labelled substrate, or by absence of or change in mobility of bands of fluorescence or color development with use of fluorogenic or chromogenic substrates, respectfully.

Quantitative densitometry can be performed with zymograms by placing the gel directly on an activated plate of a Molecular Dynamics phosphorimager (Molecular Dynamics, 928 East Arques Ave., Sunnyvale, Calif. 94086), or with a Datacopy G8 plate scanner attached to a MacIntosh computer equipped with an 8-bit videocard and McImage (Xerox Imaging Systems). Background measurements, areas of the gel separate from sample lanes, can similarly be scanned, and values subtracted from the readings for enzyme activities.

Another electrophoretically-based technique for analysis of a biological sample for presence of specific proteins is an affinity-based mobility alteration system (Lander, A. (1991) *Proc. Natl. Acad. Sci. U.S.*, 88(7):2768–2772). An MMP or other type of enzyme of interest might be detected, for example, by inclusion of a substrate analog that binds essentially irreversibly to the enzyme, hence decreasing the mobility. The affinity material is present during electrophoresis, and is incorporated into the matrix, so that detection of the enzyme of interest occurs as a result of alteration of mobility in contrast to mobility in the absence of the material. Yet another technique of electrophoretic protein separation is based on the innate charge of a protein as a function of the pH of the buffer, so that for any protein species, there exists a pH at which that protein will not migrate in an electric field, or the isoelectric point, designated pI. Proteins of a biological sample, such as a urine sample, may be separated by isoelectric focussing, then developed by assaying for enzymatic activity for example by transfer to material with substrate, i.e., zymography. Electrophoresis is often used as the basis of immunological detections, in which the separation step is followed by physical or electrophoretic transfer of proteins to an inert support such as paper or nylon (known as a "blot"), and the blotted pattern of proteins may be detected by use of a specific primary binding (Western blot) by an antibody followed by development of bound antibodies by secondary antibodies bound to a detecting enzyme such as horse radish peroxidase. Additional immunological detection systems for TRAC enzyme complexes are now described in detail below.

The term "antibody" as used herein is intended to include fragments thereof which are also specifically reactive with one of the components in the methods and kits of the invention. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The term "antibody" is further intended to include single chain, bispecific and chimeric molecules. The term "antibody" includes possible use both of monoclonal and polyclonal antibodies (Ab) directed against a target, according to the requirements of the application.

Polyclonal antibodies can be obtained by immunizing animals, for example rabbits or goats, with a purified form of the antigen of interest, or a fragment of the antigen containing at least one antigenic site. Conditions for obtaining optimal immunization of the animal, such as use of a particular immunization schedule, and using adjuvants e.g. Freund's adjuvant, or immunogenic substituents covalently attached to the antigen, e.g. keyhole limpet hemocyanin, to enhance the yield of antibody titers in serum, are well-known to those in the art. Monoclonal antibodies are prepared by procedures well-known to the skilled artisan, involving obtaining clones of antibody-producing lymphocyte, i.e. cell lines derived from single cell line isolates, from an animal, e.g. a mouse, immunized with an antigen or antigen fragment containing a minimal number of antigenic determinants, and fusing said clone with a myeloma cell line to produce an immortalized high-yielding cell line. Many monoclonal and polyclonal antibody preparations are commercially available, and commercial service companies that offer expertise in purifying antigens, immunizing animals, maintaining and bleeding the animals, purifying sera and IgG fractions, or for selecting and fusing monoclonal antibody producing cell lines, are available.

Specific high affinity binding proteins, that can be used in place of antibodies, can be made according to methods known to those in the art. For example, proteins that bind specific DNA sequences may be engineered (Ladner, R. C., et. al., U.S. Pat. No. 5,096,815), and proteins that bind a variety of other targets, especially protein targets (Ladner, R. C., et. al., U.S. Pat. No. 5,233,409; Ladner, R. C., et al., U.S. Pat. No. 5,403,484) may be engineered and used in the present invention for covalent linkage to a chelator molecule, so that a complex with a radionuclide may be formed under mild conditions. Antibodies and binding proteins can be incorporated into large scale diagnostic or assay protocols that require immobilizing the compositions of the present invention onto surfaces, for example in multi-well plate assays, or on beads for column purifications.

General techniques to be used in performing various immunoassays are known to those of ordinary skill in the art. Moreover, a general description of these procedures is provided in U.S. Pat. No. 5,051,361 which is incorporated herein by reference, and by procedures known to the skilled artisan, and described in manuals of the art (Ishikawa, E., et. al. (1988) *Enzyme Immunoassay* Igaku-shoin, Tokyo, NY; Hallow, E. and D. Lane, *Antibodies: A Laboratory Manual*, CSH Press, NY). Examples if several immunoassays are given discussed here.

Radioimmunoassays (RIA) utilizing radioactively labeled ligands, for example, antigen directly labeled with $^3$H, or $^{14}$C, or $^{125}$I, measure presence of MMP's as antigenic material. A fixed quantity of labeled MMP antigen competes with unlabeled antigen from the sample for a limited number of antibody binding sites. After the bound complex of labeled antigen-antibody is separated from the unbound (free) antigen, the radioactivity in the bound fraction, or free fraction, or both, is determined in an appropriate radiation counter. The concentration of bound labeled antigen is inversely proportional to the concentration of unlabeled antigen present in the sample. The antibody to MMP can be in solution, and separation of free and bound antigen MMP can be accomplished using agents such as charcoal, or a second antibody specific for the animal species whose immunoglobulin contains the antibody to MMP. Alternatively, antibody to MMP can be attached to the surface of an insoluble material, which in this case, separation of bound and free MMP is performed by appropriate washing.

Immunoradiometric assays (IRMA) are immunoassays in which the antibody reagent is radioactively labeled. An IRMA requires the production of a multivalent MMP conjugate, by techniques such as conjugation to a protein e.g., rabbit serum albumin (RSA). The multivalent MMP conjugate must have at least 2 MMP residues per molecule and the MMP residues must be of sufficient distance apart to allow binding by at least two antibodies to the MMP. For example, in an IRMA the multivalent MMP conjugate can be attached to a solid surface such as a plastic sphere. Unlabeled "sample" MMP and antibody to MMP which is radioactively labeled are added to a test tube containing the multivalent MMP conjugate coated sphere. The MMP in the sample competes with the multivalent MMP conjugate for MMP antibody binding sites. After an appropriate incubation period, the unbound reactants are removed by washing and the amount of radioactivity on the solid phase is determined. The amount of bound radioactive antibody is inversely proportional to the concentration of MMP in the sample.

Other immunoassay techniques use enzyme labels such as horseradish peroxidase, alkaline phosphatase, luciferase, urease, and β-galactosidase. For example, MMP's conjugated to horseradish peroxidase compete with free sample MMP's for a limited number of antibody combining sites present on antibodies to MMP attached to a solid surface such as a microtiter plate. The MMP antibodies may be attached to the microtiter plate directly, or indirectly, by first coating the microtiter plate with multivalent MMP conjugates (coating antigens) prepared for example by conjugating MMP with serum proteins such as rabbit serum albumin (RSA). After separation of the bound labeled MMP from the unbound labeled MMP, the enzyme activity in the bound fraction is determined colorimetrically, for example by a multi-well microtiter plate reader, at a fixed period of time after the addition of horseradish peroxidase chromogenic substrate.

Alternatively, the antibody, attached to a surface such as a microtiter plate or polystyrene bead, is incubated with an aliquot of the biological sample. MMP present in the fluid will be bound by the antibody in a manner dependent upon the concentration of MMP and the association constant between the two. After washing, the antibody/MMP complex is incubated with a second antibody specific for a different epitope on MMP distal enough from the MMP-specific antibody binding site such that stearic hindrance in binding of two antibodies simultaneously to MMP may be accomplished. For example, the second antibody may be specific for a portion of the proenzyme sequence. The second antibody can be labeled in a manner suitable for detection, such as by radioisotope, a fluorescent compound or a covalently linked enzyme. The amount of labeled secondary antibody bound after washing away unbound secondary antibody is proportional to the amount of MMP present in the biological sample.

The above examples of immunoassays describe the use of radioactively and enzymatically labeled tracers. Assays also may include use of fluorescent materials such as fluorescein and analogs thereof, 5-dimethylaminonaphthalene-1-sulfonyl derivatives, rhodamine and analogs thereof, coumarin analogs, and phycobiliproteins such as allophycocyanin and R-phycoerythrin; phosphorescent materials such as erythrosin and europium; luminescent materials such as luminol and luciferin; and sols such as gold and organic dyes. In one embodiment of the present invention, the biological sample is treated to remove low molecular weight contaminants.

In one embodiment of the present invention, the biological sample is treated to remove low molecular weight contaminants, for example, by dialysis. By the term "dialysis" this invention includes any technique of separating the enzymes in the sample from low molecular weight contaminants. The Examples use Spectra/Por membrane dialysis tubing with a molecular weight cut-off (MWCO) of 3,500, however other products with different MWCO levels are functionally equivalent. Other products include hollow fiber concentration systems consisting of regenerated cellulose fibers (with MWCO of 6,000 or 9,000) for larger volumes; a multiple dialyzer apparatus with a sample size for one to 5 ml; and multiple microdialyzer apparatus, convenient for samples in plates with 96 wells and MWCOs at 5,000, 8,000 and 10,000, for example. These apparatuses are available from PGC Scientific, Gaithersburg, Md., 20898. Those with skill in the art will appreciate the utility of multiple dialysis units, and especially suitable for kits for reference lab and clinic usage. Other equivalent techniques include passage through a column holding a resin or mixture of resins suitable to removal of low molecular weight materials. Resins such as BioGel (BioRad, Hercules, Calif.) and Sepharose (Pharmacia, Piscataway, N.J.) and others are well-known to the skilled artisan. The technique of dialysis, or equivalent techniques with the same function, are intended to remove low molecular weight contaminants from the biological fluids. While not an essential component of the present invention, the step of removal of such contaminants facilitates detection of the disorder-associated enzymes in the biological samples.

The invention is further illustrated by the following examples, which should not be construed as further limiting. The contents of all references, pending patent applications and published patents, cited throughout this application are hereby expressly incorporated by reference.

EXAMPLES

The following materials and methods were used throughout these Examples, set forth below.

Materials and Methods

Urine Sample Collection and Preparation—Urine sample collection was performed as described in Moses, M. A., et al. (1998) Cancer Res. 58:1395–9, the contents of which are herein incorporated by reference in their entirety. Samples were immediately frozen after collection and stored frozen at −20° C. until assay. Prior to analysis, specimens containing blood or leukocytes were excluded by testing for the presence of blood and leukocytes using Multistix 9 Urinalysis Strips (Bayer, Elkhart, Ind.). The creatine concentrations of urine samples were determined using a commercial kit (Sigma Chemical Co., St. Louis, Mo.) according to manufacturer's instructions.

Substrate Gel Electrophoresis—Substrate gel electrophoresis was performed based on a previously described in U.S. Ser. No. 09/469,637 with modifications. Original urine samples (50 µl) were mixed with non-reducing sample buffer [4% sodium dodecyl sulfate (SDS), 0.15 M Tris pH 6.8, 20% v/v glycerol, and 0.5% v/v bromphenol blue] and were separated on a 10% polyacrylamide gel containing 0.1% gelatin (Bio-Rad, Hercules, Calif.). After electrophoresis, gels were washed twice with 2.5% Triton X-100 (15 minutes/each wash). Substrate digestion was carried out by incubating the gel in 50 mM Tris-HCl (pH 7.6) containing 5 mM $CaCl_2$, 1 µM $ZnCl_2$, 1% Triton X-100, and 0.02% $NaN_3$ at 37° C. for 24hours. The gel was stained with 0.1% Coomassie Brilliant Blue R250 (BioRad, Hercules, Calif.), and the location of gelatinolytic activities were detected as clear bands on the background of a uniform blue staining.

Protein Electrophoresis and Western Blot Analysis—Urine samples were concentrated using an UltraFree-4 centrifugal filter device with molecular weight cut off (MWCO) of 50 kDa (Millipore, Bedford, Mass.). Protein concentrations of the concentrated urine samples were determined using the MicroBCA method (Pierce, Rockford, Ill. 61105). Equal amount of proteins (20 µg) was loaded onto 4–15% gradient gels and separated by SDS-PAGE under non-reducing conditions. Resolved proteins were electrophoretically transferred to nitrocellulose membranes (TransBlot, Bio-Rad, Hercules, Calif.). The membranes were blocked with 5% low fat dry milk in TBS-T (10 mM Tris, pH 7.2, 50 mM NaCl, 0.5% Tween 20) for 1 hour at room temperature, followed by incubating with primary antibody at 4° C. for 18 hours. Blots were washed 8 times with TBS-T (5 minutes/wash) and incubated with 1:5000 dilution of horseradish peroxidase (HRP) conjugated secondary antibody (Vector Laboratories, Burlingame, Calif.) diluted in TBS-T containing 3% BSA for 1 hour at room temperature. Labeled proteins were visualized with enhanced chemiluminescence (Amersham, Arlington Heights, Ill.). Purified polyclonal antibodies against human NGAL were used at 1:100 dilution (Kjeldsen, L., et al. (1993)). Purified human neutrophil MMP-9/NGAL complex was used as positive control (Cal-Biochem, La Jolla, Calif.).

Immunoprecipitation—Original urine samples containing the 125 kDa MMP activity were mixed with equal volumes of RIPA buffer (150 mM NaCl, 1.0% NP-40, 0.5% sodium deoxycholate, 0.1% SDS, 50 mM Tris pH 8.0, 0.02% sodium azide). 50 µl diluted urine samples were mixed with increasing amount of the rabbit anti-human NGAL antibody or a control antibody. After incubating on ice for thirty minutes, samples were mixed with 5 µl RIPA-buffered Zysorbin (ZyoMed Laboratories, South San Francisco, Calif.). Followed an additional incubation on ice for thirty minutes, the antibody-antigen complexes were removed with a centrifugation at 10,000 g for 5 minutes. The supernatants were subjected to substrate gel electrophoresis to detect the remaining MMP activities.

In Vitro Reconstitution of MMP-NGAL Complexes—Recombinant human proMMP-9 (Oncogene, Cambridge, Mass.) was diluted with gelatinase buffer [50 mM Sodium Acetate (pH=5.5) or 50 mM Tris-HCl (pH=7.0, 7.6, or 8.0) containing 5 mM $CaCl_2$, 1 µM $ZnCl_2$], to a final concentration of 10 µM. Recombinant human NGAL was purified as previously described and was diluted to 70 µM in the gelatinase buffer. ProMMP-9 was mixed with NGAL in a molar ratio of 1:20 and was incubated at 37° C. for one hour. The formation of MMP-9/NGAL complex was analyzed using substrate gel electrophoresis. ProMMP-9 and NGAL were also individually diluted in normal control urine with no MMP activity. The possibility of MMP-9/NGAL complex formation in urine was investigated by mixing proMMP-9 and NGAL in moral ratios of 2:1, 1:5, 1:10 and 1:20. MMP-9/NGAL complex was detected using substrate gel electrophoresis.

Example 1

Substrate Gel Electrophoresis of MMP Activities in Urine Samples

Figure 1:
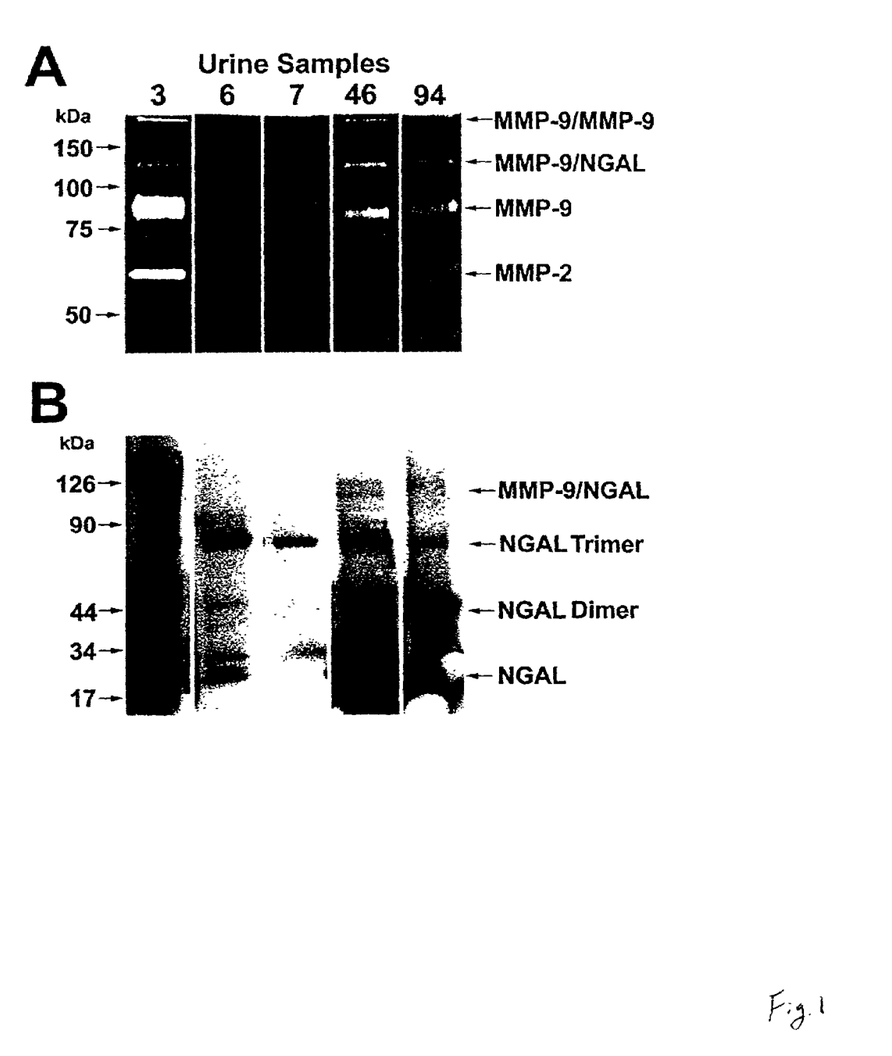

MMP activities contained in urine samples were assayed using substrate gel electrophoresis. 50 µl of freshly thawed urine sample was used for analysis. At least four major MMP activities were readily detected in these urine samples, with apparent molecular mass of 200,000, 125,000, 92,000, and 72,000 (FIG. 1A). The 92 kDa and the 72 kDa MMP activities have previously been determined to be MMP-9 and MMP-2 respectively.

Figure 2:
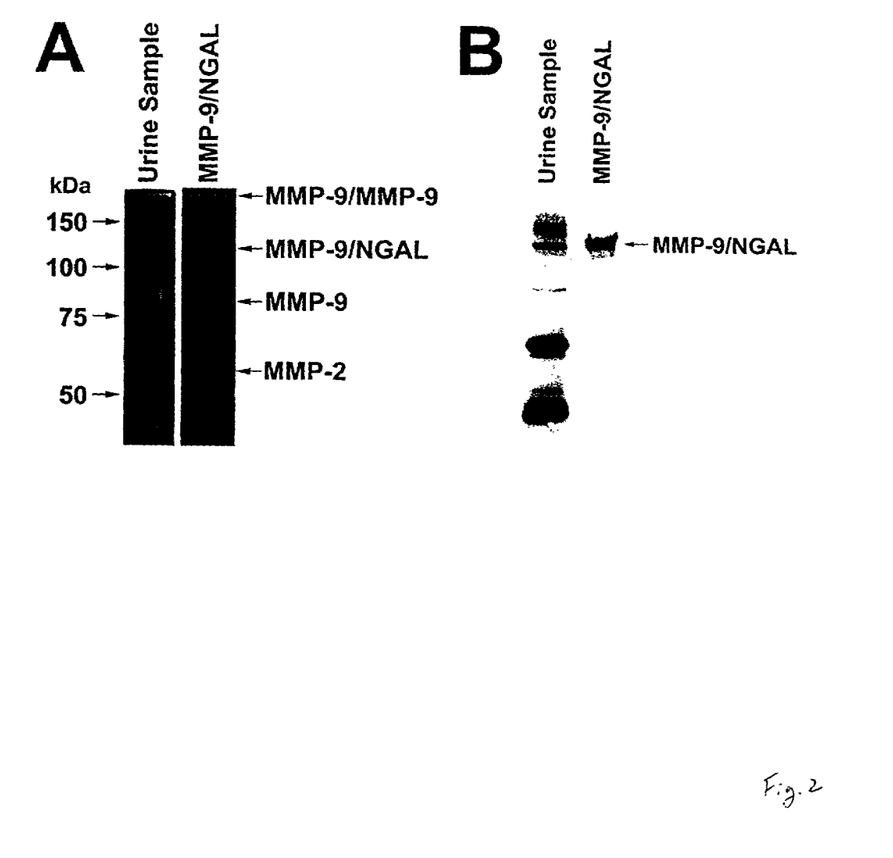
FIG. 2 shows a Western blot and substrate gel electrophoresis of urine samples and purified human neutrophil MMP-9/NGAL complex. A. NGAL Western blot analysis: A concentrated urine sample containing the 125 kDa MMP activity, together with purified human neutrophil MMP-9/NGAL, were separated by 4–15% SDS-gel electrophoresis under non-reducing conditions, and subsequently subjected to Western blot analysis using a polyclonal antibody against human NGAL. The 125 kDa MMP-9/NGAL complex is marked (arrow on right). B. Substrate gel electrophoresis: The same urine sample and purified human neutrophil MMP-9/NGAL complex were analyzed with substrate gel electrophoresis. The positions of MMP-9 dimer (200 kDa), MMP-9/NGAL (125 kDa), MMP-9 (92 kDa), and MMP-2 (72 kDa) are denoted with arrows on right. The molecular size markers are Perfect Protein Markers (Novagen, Madison, Wis.) with sizes of 150 kDa, 100 kDa, 75 kDa, and 50 kDa (arrows on left).

The 200 kDa MMP activities is in correspondence with the predicted molecular size of MMP-9 dimer. The identity of the 125 kDa MMP is unclear. When analyzed together with purified human MMP-9/NGAL complex from neutrophil, the 125 kDa urinary MMP activity migrated in the same position as that of human neutrophil MMP-9/NGAL (FIG. 2A). This 125 kDa urinary MMP is an active complex of MMP-9 and NGAL. The identity of these gelatinolytic activities of being MMPs was confirmed by inhibition studies using 1,10-phenanthroline at a final concentration of 10 mM (data not shown).

Example 2

Western Blot Analysis of Urine Samples with anti-NGAL Antibody

To further demonstrate the identity of the 125 kDa urinary MMP as a complex of MMP-9 and NGAL, concentrated urine samples were subjected to Western blot analysis using a purified antibody against human NGAL (Kjeldsen, L. (1993)). Under non-reducing conditions, a protein band of 125 kDa was detected in urine samples containing the 125 kDa MMP activity (FIG. 1B). Screening of urine samples from cancer patients established a correlationship between the detection of MMP-9/NGAL protein complex and the presence of the 125 kDa MMP activity (FIG. 1B). Using the purified anti-NGAL antibody, a 125 kDa protein band was consistently detected in urine samples containing the 125 kDa MMP activity. The antibody also detected the presence of NGAL monomer (25 kDa), dimer (50 kDa), and trimer forms (75 kDa) in all of the urine samples analyzed. The specificity of the NGAL antibody was confirmed using purified human neutrophil MMP-9/NGAL complex. Under non-reducing conditions, the antibody recognized the 125 kDa MMP-9/NGAL complex in the concentrated urine sample, as well as the MMP-9/NGAL complex purified from neutrophil (FIG. 2B). In addition to the MMP-9/NGAL complex and the NGAL monomer, dimer and trimer complexes, several minor protein bands with approximate molecular sizes of 150 kDa were also detected in the concentrated urine sample. Although their identities are currently unclear, they are most likely to be proteins that non-specifically cross-reacted with anti-NGAL antibody.

Example 3

Immunoprecipitation-Zymography

Figure 3:
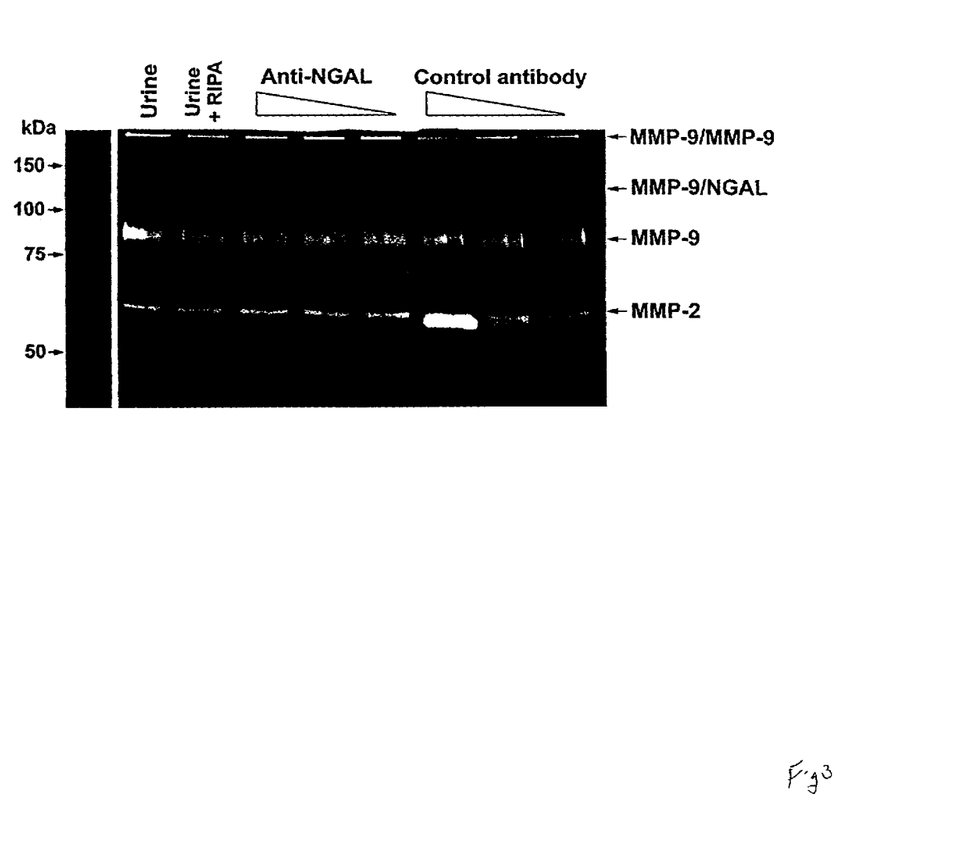
FIG. 3 shows an immunoprecipitation of the 125 kDa MMP activity using anti-NGAL antibody. 50 μl of urine samples (1:1 v/v diluted with RIPA) containing the 125 kDa MMP activity were mixed with 1.0, 0.1 or 0.01 μl of anti-NGAL antibody or a control antibody. After incubating on ice for thirty minutes, the antibody-antigen complexes were removed using Zysorbin. The supernatants were subjected to substrate gel electrophoresis to detect the remaining MMP activities. The increased MMP-2 activity observed in the sample treated with 1.0 μl of the control antibody was the endogenous MMP-2 activity from the serum.

To further verify the identity of the 125 kDa MMP activity in urine, anti-NGAL antibody was used to immunoprecipitate any MMP activities that exist in the complex form with NGAL in urine. As shown in FIG. 3, anti-NGAL antibody specifically immunoprecipitated the 125 kDa urinary MMP activity, in a concentration-dependent manner. Increasing amounts of the 125 kDa urinary MMP activity was removed by the treatment with increasing amounts of anti-NGAL antibody. When treated with 1.0 µl of anti-NGAL antibody, the 125 kDa MMP activity was completely removed. The anti-NGAL antibody had no effect on any other MMP activities, e.g., the 200 kDa MMP-9 dimer, the 92 kDa MMP-9, or the 72 kDa MMP-2. The specificity of immunoprecipitation was also confirmed using a control antibody which did not immunoprecipitate any of the MMP activities, even at the highest concentration. The increase in MMP-2 activity in the sample treated with 1.0 µl of control antibody resulted from endogenous MMP-2 activity contained in the serum. Taken together these data support our finding that the 125 kDa MMP activity in urine samples of cancer patients is a complex of MMP-9 and NGAL.

Example 4

Re-constitution of MMP-9/NGAL Complex In Vitro

Figure 4:
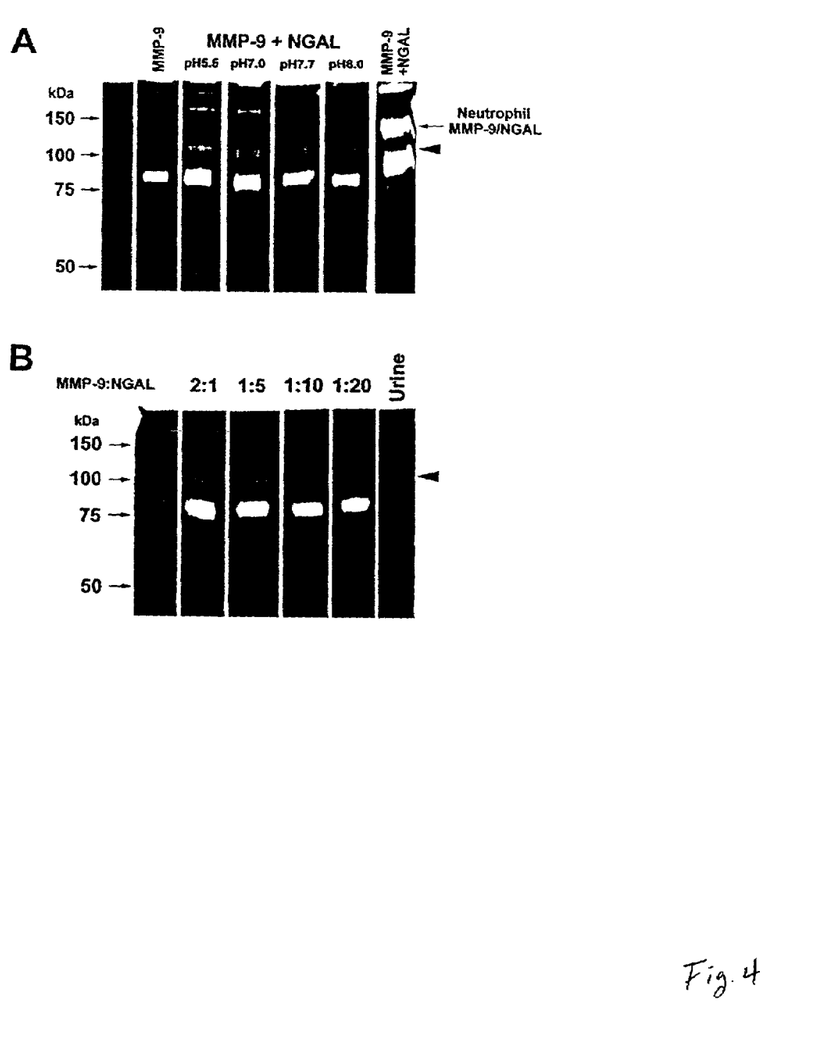

The formation of MMP-9/NGAL complex was first investigated using gelatinase buffer that contains cationic ions. Recombinant human proMMP-9 and human NGAL were first diluted in gelatinase buffers with different pH values (5.5, 7.0, 7.6 and 8.0). Diluted proMMP-9 and NGAL were subsequently mixed in a molar ratio of 1:10, to final concentrations of 2.6 µM and 26 µM respectively. After one hour incubation at 37° C., the formation of MMP-9/NGAL complexes was monitored using substrate gel electrophoresis. Mixing proMMP-9 and NGAL generated a predominant MMP activity with a molecular size of approximately 115 kDa (FIG. 4A). Formation of the 115 kDa MMP-9/NGAL complex occurred in buffers with pH values ranging from 5.5 to 8.0, the pH range of normal urine. However, the size of this predominant MMP activity is not the same as that of purified human neutrophil MMP-9/NGAL. There is a minor MMP activity of 125 kDa, observed in pH 7.0, 7.6 and 8.0 buffers. The possibility of MMP-9/NGAL complex formation in urine was directly studied by diluting proMMP-9 and NGAL in normal control urine. Diluted proMMP-9 and NGAL were mixed in different molar ratios (proMMP-9/NGLA 2:1, 1:5, 1:10 and 1:20) and incubated at 37° C. for one hour. The formation of a 115 kDa MMP-9/NGAL complex was readily detected in all mixing ratios (FIG. 4B). No MMP activity was detected in the control urine used as a diluent.

Example 5

Modulation of MMP-9 Degradation by NGAL in Vitro

The effect of NGAL on MMP-9 degradation in vitro was studied by mixing MMP-9 (0.1µ) and NGAL (1/0µ) prior to incubation. MMP-9 degradation was inhibited in the presence of NGAL resulting in a decrease in the enzymatic degradation rate as evidenced by an increase in the remaining amounts of enzyme at each time point compared with MMP-9 incubated by itself. Immunodepleted NGAL had no apparent protection of MMP-9. In the presence of increasing amount of NGAL, degradation of MMP-9 decreased and resulted in an increase in the remaining MMP-9 activity. NGAL appears to be capable of protecting MMP-9 from degradation in a dose-dependent manner, resulting in the preservation of MMP-9 activity. These data suggest a potential regulatory role for NGAL in modulating MMP-9 activity, for example, NGAL may be involved in tumor progression via its interaction with MMP-9.

Example 6

Modulation of MMP-9 Degradation by NGAL In Cell Culture

The protective effect of NGAL on MMP-9 degradation was studied in cell culture using MDA-MB-231 human breast carcinoma cells. MMP-9 activity was detected in cells overexpressing NGAL (N-2 and N-5). Thus, it appeared that elevated NGAL expression resulted in an increase in MMP-9 activity. Steady state MMP-9 mRNA levels were determined using RT-PCT analysis and no apparent differences were detected. Expression levels of endogenous MMP-9 inhibitor, TIMP-1, and a house-keeping gene, GAPGH, were determined and overexpression of NGAL had no apparent influence on mRNA levels of TIMP-1 or GAPDH. Overexpression of NGAL in human breast carcinoma cells resulted in an increase in MMP-9 activity independent of changes in MMP-9 gene transcription.

DISCUSSION

Identification of hMW enzyme complexes in the urine of cancer patients, e.g., enzyme complexes comprising MMP-9 and NGAL, is predictive of TRAC and is supported by the following findings: (a) the 125 kDa MMP activity in urine migrates at the same position as human neutrophil MMP-9/NGAL does; (b) anti-NGAL antibody successfully detected a 125 kDa protein band in most of the concentrated urine samples that contain the 125 kDa MMP activity; (c) the same antibody was able to specifically immunoprecipitate the 125 kDa MMP activity in urine in a concentration-dependent manner, without affecting any other MMP activities. Such evidence agrees with the findings described in U.S. Ser. No. 09/469,637, which is incorporated herein by reference in its entirety, that the detection of hMW MMPs, as well as MMP-9 and MMP-2, serves as independent predictors of metastatic or organ-confined cancers, respectively.

NGAL was first identified as a 25 kDa protein that was co-purified with human neutrophil gelatinase (Kjeldsen, L., et al. (1993) J Biol Chem. 268: 10425–32). Binding of NGAL and MMP-9 results in a gelatinase activity of 135 kDa detected in specific granules of human neutrophil stimulated with phorbol myristate acetate (PMA) (Kjeldsen, L. et al. (1993)). NGAL and MMP-9 are stored in specific granules, while MMP-9 is also present independently in gelatinase granules (Morel, F., et al., (1994) Biochim Biophys Acta. 1201: 373–80; Kjeldsen, L., et al. (1994) Blood. 83: 799–807; and Borregaard, N. and Cowland, J. B. (1997) Blood. 89: 3503–21). However, the MMP-9/NGLA complex detected in urine of cancer patients are not derived from leukocytes since we have specifically excluded the urine samples that contain leukocytes.

Interestingly, human NGAL contains sequence similarities to mouse 24p3 and rat neu/HER2/c-erbB-2 related lipocalin (NRL), both overexpressed in oncogene mediated cell transformation (Cowland, J. B. and Borregaard, N. (1997) Genomics. 45: 17–23; Hraba-Renevey, S., et al. (1989) Oncogene. 4: 601–8; Stoesz, S. P. and Gould, M. N. (1995) Oncogene. 11: 2233–41). Under normal conditions, expression of human NGAL is restricted to breast, lung, trachea, and bone marrow (Cowland, J. B. and Borregaard, N. (1997) Genomics. 45: 17–23; Stoesz, S. P., et al. (1998) Int. J Cancer. 79: 565–72). However, elevated levels of NGAL expression has been observed in human breast tumors as well as in adenocarcinomas of lung, colon and pancreas (Stoesz (1998); Friedl, A., et al.(1999) Histochem J. 31: 433–41). An increased production of NGAL can be closely associated with cancer disease status, which subsequently contribute to the elevated levels of MMP-9/NGAL complex in urine. This complex can be detected with substrate gel electrophoresis as well as antibody-based assays. As described in U.S. Ser. No. 09/469,637, the presence of the 125 kDa MMP activity in urine can serve as an independent multivariate predictor of cancer metastasis, the identification of this activity as MMP-9/NGAL complex will facilitate the development of a non-invasive prognosis tool to assess disease status of various cancers.

The origin of the 125 kDa MMP-9/NGAL activity in urine of cancer patients remains unclear. Given that the glomerular filtration limit is only 45 kDa, it is unlikely that this large protein complex is directly filtered from serum into urine. The possibility that MMP-9/NGAL complex forms after each component was separately filtrated into urine was investigated using in vitro reconstitution assay. The results demonstrate the feasibility of MMP-9/NGAL complex formation in gelatinase buffers with different pH values, as well as, in normal urine. Therefore, it is likely that MMP-9 and NGAL are separately executed into urine where they form the 125 kDa MMP-9/NGAL complex.

The existence of MMP-9 and NGAL complex in urine was supported by a recent independent study (Monier, F., Clin Chim Acta. 299: 11–23, 2000). Under reducing conditions, MMP-9 and NGAL were separately detected in a continuous-elution electrophoresis fraction that contains a 115 kDa gelatinase activity. The detection of MMP-9 and NGAL in the same fraction shows the observed 115 kDa gelatinase activity as a complex of MMP-9 and NGAL.

Recent studies have also confirmed that NGAL appears to exert a protective effect on MMP-9 and prevents MMP-9 from degradation both in vitro and in cells. Examples 5 and 6 suggest that the MMP-9-NGAL complex likely plays an active role in tumor progression.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A non-invasive method for facilitating the diagnosis of a subject for a tissue remodeling-associated condition, comprising:
   obtaining a urine sample from a subject;
   contacting the urine sample with an antibody specifically reactive with NGAL to detect an MMP-9/NGAL complex in the urine sample;
   wherein the presence of the MMP-9/NGAL complex indicates the presence of a tissue remodeling-associated condition, thereby facilitating the diagnosis of the subject for a tissue remodeling-associated condition.

2. The method of claim 1, wherein the tissue remodeling-associated condition is cancer.

3. The method of claim 2, wherein the cancer is in cells of epithelial origin.

4. The method of claim 3, wherein the cancer is selected from the group consisting of cancers of the nervous system, breast, prostate, retina, lung, skin, kidney, liver, pancreas, genito-urinary tract, and gastrointestinal tract.

5. The method of claim 2, wherein the cancer appears in cells of endodermal origin.

6. The method of claim 2, wherein the cancer affects cells of bone or of hematopoietic origin.

7. The method of claim 1, further comprising removal of contaminants from the urine prior to the detection step.

8. The method of claim 7, wherein the urine is dialyzed.

9. The method of claim 1, wherein the MMP-9/NGAL complex is detected by a radio-immunoassay.

10. The method of claim 1, wherein the MMP-9/NGAL complex is detected by an enzyme-linked immunoabsorbant assay.

* * * * *